(12) United States Patent
Sprague (10) Patent No.: US 9,927,369 B2
(45) Date of Patent: Mar. 27, 2018

(54) AUTOMATED DEFECT DETECTION AND MAPPING FOR OPTICAL FILTERS

(71) Applicant: Materion Corporation, Mayfield Heights, OH (US)

(72) Inventor: Robert Sprague, Acton, MA (US)

(73) Assignee: MATERION CORPORATION, Mayfield Heights, OH (US)

( * ) Notice: Subject to any disclaimer, the term of this patent is extended or adjusted under 35 U.S.C. 154(b) by 29 days.

(21) Appl. No.: 15/172,592

(22) Filed: Jun. 3, 2016

(65) Prior Publication Data
US 2016/0356724 A1    Dec. 8, 2016

Related U.S. Application Data

(60) Provisional application No. 62/170,310, filed on Jun. 3, 2015.

(51) Int. Cl.
*G01N 21/88* (2006.01)
*G01M 11/02* (2006.01)
(Continued)

(52) U.S. Cl.
CPC ..... *G01N 21/8806* (2013.01); *G01M 11/0285* (2013.01); *G01N 21/958* (2013.01);
(Continued)

(58) Field of Classification Search
CPC ............. G01N 21/8806; G01N 21/958; G01N 21/255; G01N 2201/061; G01N 2021/9511; G01N 2201/068; G01M 11/0285
See application file for complete search history.

(56) References Cited

U.S. PATENT DOCUMENTS 6,088,112 A    7/2000  Lee et al.
7,068,430 B1   6/2006  Clarke et al.
(Continued)

FOREIGN PATENT DOCUMENTS

EP    0 515 273 A1    11/1992
EP    0 711 988 A2    5/1996
(Continued)

OTHER PUBLICATIONS

International Search Report and Written Opinion for International Application No. PCT/US2016/035697 dated Sep. 26, 2016.

*Primary Examiner* — Sang Nguyen
(74) *Attorney, Agent, or Firm* — Richard M. Klein; Fay Sharpe LLP (57) ABSTRACT

Devices and methods are disclosed for characterizing point flaws (including pinholes and point defects) of an optical filter. A passband test is performed, including: illuminating the optical filter with passband illumination whose spectral range at least overlaps a passband of the optical filter; acquiring a passband map of the optical filter using a two-dimensional array of photodetectors while illuminating the optical filter with the passband illumination; and identifying point defects of the optical filter as low intensity locations of the passband map. A stopband test is performed, including: illuminating the optical filter with stopband illumination whose spectral range lies entirely outside of the passband of the optical filter; acquiring a stopband map of the optical filter using the two-dimensional array of photodetectors while illuminating the optical filter with the stopband illumination; and identifying pinholes of the optical filter as high intensity locations of the stopband map.

19 Claims, 5 Drawing Sheets

(51) Int. Cl.
 *G01N 21/958* (2006.01)
 *G01N 21/25* (2006.01)
 *G01N 21/95* (2006.01)

(52) U.S. Cl.
 CPC .... *G01N 21/255* (2013.01); *G01N 2021/9511* (2013.01); *G01N 2201/061* (2013.01); *G01N 2201/068* (2013.01)

(56) References Cited

U.S. PATENT DOCUMENTS

| | | | | |
|---|---|---|---|---|
| 8,958,156 | B1* | 2/2015 | Erdogan | G02B 5/28 359/583 |
| 2003/0184741 | A1 | 10/2003 | Ueta | |
| 2007/0247619 | A1* | 10/2007 | Wong | G01N 21/958 356/239.2 |
| 2009/0097030 | A1* | 4/2009 | Ho | G01N 21/958 356/418 |
| 2009/0177428 | A1* | 7/2009 | Iden | G01B 11/26 702/94 |
| 2009/0190134 | A1 | 7/2009 | Shirai et al. | |
| 2009/0303468 | A1* | 12/2009 | Itoh | G01B 11/306 356/237.2 |
| 2012/0147468 | A1* | 6/2012 | Bell | G02B 5/201 359/491.01 |
| 2014/0299745 | A1 | 10/2014 | Yadid-Pecht et al. | |

FOREIGN PATENT DOCUMENTS

| | | |
|---|---|---|
| JP | H06-208017 | 7/1994 |
| JP | 2010 256 113 A | 11/2010 |

\* cited by examiner

AUTOMATED DEFECT DETECTION AND MAPPING FOR OPTICAL FILTERS

This application claims the benefit of U.S. Provisional Application No. 62/170,310 filed Jun. 3, 2015 and titled "AUTOMATED DEFECT DETECTION AND MAPPING FOR OPTICAL FILTERS". U.S. Provisional Application No. 62/170,310 filed Jun. 3, 2015 is incorporated herein by reference in its entirety.

BACKGROUND

The following relates to the optical filter arts, optical characterization arts, and related arts, and to applications using same.

Optical filters are used in a wide range of optical applications, such as astronomy, still and video cameras and other imaging devices, televisions, computer monitors, cellular telephone screens, and other display devices, optical sensors such as motion sensors, gesture sensors, and the like, and so forth. Depending on the application, such filters can range in size up to a square meter or larger in area. Within a design-basis optical spectrum an optical filter generally has a passband for which the filter transmits light, and a stopband (or blocking band) for which the filter does not transmit light. In a bandpass filter, the passband is usually relatively narrow and most of the design-basis optical spectrum lies outside of the passband and is blocked. Passband filters with two or more separate passbands are also known. In a low-pass or high-pass filter, the passband includes all wavelengths of the design-basis spectrum below (or above) a cutoff wavelength or frequency. Filters can be further optically characterized by parameters such as the transmission in the passband and the stopband, passband full-width-at-half-maximum (FWHM), the slope of the transition at the edge(s) between the passband and the stopband, and so forth.

Optical filters can employ various designs. A common type of optical filter is an interference filter, in which a stack of optical layers are arranged with thicknesses and refractive indices that are precisely designed so that reflected and transmitted light rays within the stack constructively combine within the passband and destructively combine in the stopband. An interference filter can provide steep passband edges, high passband transmission (approaching 99% or higher) and very low transmission in the stopband (near 0% transmission). The stack of layers is typically formed on an optically transparent substrate (e.g. glass) by a technique such as sputter deposition, thermal vacuum evaporation, or the like which is performed in a vacuum chamber or other controlled atmosphere.

The manufactured filter is typically visually inspected for defects, and its filter characteristics are measured, usually by spectral measurement over the design-basis wavelength range, to confirm the filter specification is met (e.g. passband center wavelength and FWHM, cutoff slope, et cetera). Filter characterization is usually performed for each manufactured filter because for filters with demanding specifications filter characteristics can change significantly (enough to be out-of-specification) in response to even small errors in layer thicknesses or refractive indices. Since thickness non-uniformity over the area of the filter can occur, the filter spectral characterization may be repeated at several different areas. Those filters which pass inspection and meet the filter specification are delivered to the customer, or alternatively may first be mounted in a filter frame or optical sub-system before delivery.

Some improvements are disclosed herein.

BRIEF DESCRIPTION

In some illustrative embodiments disclosed herein, a test device is disclosed for characterizing point flaws of an optical filter under test including pinholes and point defects. The test device comprises: a passband illumination source configured to illuminate the optical filter under test with passband illumination whose spectral range at least overlaps a passband of the optical filter under test; a stopband illumination source configured to illuminate the optical filter under test with stopband illumination whose spectral range lies entirely outside of the passband of the optical filter under test; and a two-dimensional array of photodetectors arranged to detect the passband illumination after passing through the optical filter under test and to detect the stopband illumination after passing through the optical filter under test.

In some illustrative embodiments disclosed herein, a test method is disclosed for characterizing point flaws of an optical filter under test including pinholes and point defects. The test method comprises performing a passband test and performing a stopband test. The passband test includes illuminating the optical filter under test with passband illumination whose spectral range at least overlaps a passband of the optical filter under test, and acquiring a passband map of the optical filter under test using a two-dimensional array of photodetectors while illuminating the optical filter under test with the passband illumination, and identifying point defects of the optical filter under test as low intensity locations of the passband map. The stopband test includes illuminating the optical filter under test with stopband illumination whose spectral range lies entirely outside of the passband of the optical filter under test, and acquiring a stopband map of the optical filter under test using the two-dimensional array of photodetectors while illuminating the optical filter under test with the stopband illumination, and identifying pinholes of the optical filter under test as high intensity locations of the stopband map.

In some illustrative embodiments disclosed herein, a test device is disclosed for characterizing point flaws of an optical filter under test including pinholes and point defects. The test device comprises: an illumination source configured to illuminate the optical filter under test with passband illumination whose spectral range at least overlaps a passband of the optical filter under test; an array of photodetectors arranged to acquire a passband map of the optical filter under test while illuminating the optical filter under test with the passband illumination; an illumination source configured to illuminate the optical filter under test with stopband illumination whose spectral range lies entirely outside of the passband of the optical filter under test; wherein the array of photodetectors is further arranged to acquire a stopband map of the optical filter under test while illuminating the optical filter under test with the stopband illumination.

DETAILED DESCRIPTION

As used herein, and as is conventional in the art, terms such as "optical spectrum", "optical", "wavelength", "frequency", "light", "light beam", and so forth are not limited to the visible spectrum but rather for a given filter may extend into, or reside entirely within, the infrared and/or ultraviolet spectral regions.

It is recognized herein that existing optical filter inspection processes are not sufficient for manufacturing optical filters for some filter applications. For example, consider imaging applications using arrays of detectors (micro bolometers, CCDS, CMOS, . . . ), in which the filter is either placed in intimate contact with the array or is conjugate to it in the optical train. In these applications small defects in the filters characteristic result in loss of information at a fixed location in the image. Visual inspection for this sort of defect is both difficult and time consuming.

For optical filters, point flaws can be functionally classified into two types: pinholes and defects. A pinhole is a point at which the optical stack is not present or is defective so that it does not stop light. A pinhole may be formed due to the presence of a particle or contamination or surface roughness on the substrate prior to the stack deposition, or may be formed post-deposition as a scratch or other abrasion. Since the substrate is transparent, light passes through a pinhole regardless of whether the wavelength of the light is in the passband or the stopband. On the other hand, a defect is a particle or contaminant which occludes light in the passband (and may also occlude light in the stopband, but this is of little consequence).

As used in this context, the term "point flaw", or "pinhole", or "point defect" is intended to indicate a flawed area that is much smaller than the total area of the filter, and in particular is small enough that the point flaw would have negligible impact if the filter were used to filter a light beam having an beam cross-section area comparable to the area of the filter (e.g. 6-inch filter used to filter a 2-inch diatheter or larger light beam).

Recognizing herein that even a small number and low density of point flaws can degrade filter performance in certain applications, such as certain imaging applications, it is disclosed herein to provide a filter test specifically to assess point flaws in the filter. This test for point flaws is to be performed in addition to the conventional filter spectral characterization, and may either replace a visual inspection of the manufactured filter or be performed in addition to visual inspection (for example, it may be efficient to perform initial visual inspection to identify and discard any filters that are visibly defective before performing filter spectral characterization and the test for point flaws disclosed herein).

The disclosed test for point flaws is designed to detect both pinholes and point defects, and to distinguish between them. To do this, it applies illumination in the passband, which should transmit entirely through the optical filter. Any place where light is not transmitted is therefore a passband-point defect. To detect these point defects, a two-dimensional array is used to simultaneously measure the transmitted light across the entire area of the optical filter.

In the same manner also the test applies illumination in the stopband, which should be entirely blocked by the optical filter. Any place where light is transmitted is therefore a pinhole. To detect these pinholes, the same two-dimensional array is used (assuming it has sufficiently broadband detectors to detect light both in the passband and the stop band) to simultaneously measure the transmitted light (or lack thereof) across the entire area of the optical filter.

The disclosed test for point flaws in some embodiments employs illumination at only two wavelengths: one in the passband, and one in the stopband. This is not sufficient to perform filter spectral characterization, but it is sufficient to test for pinholes and point defects. The test for point flaws makes the following assumptions: a pinhole will pass light anywhere in the stopband, and a point defect will block light anywhere in the passband. As such, it is sufficient to perform the test using one wavelength (or a band of wavelengths) in the passband, and using one wavelength (or a band of wavelengths) in the stopband. This assumption is reasonable even if the optical filter under test has a passband comprising a plurality of discrete passband sections separated by discrete stopband sections, since a pinhole will generally pass light of any wavelength in the design-basis spectrum, and likewise a point defect will generally block light anywhere in the design-basis spectrum. This makes the test for point flaws fast, and enables use of low-cost equipment—for example, no spectrometer or spectrograph is needed. Additionally, the test could be performed for each pass or blocking band or a plurality of sources could be used to test all pass bands or blocking bands simultaneously as required.

Figure 1:
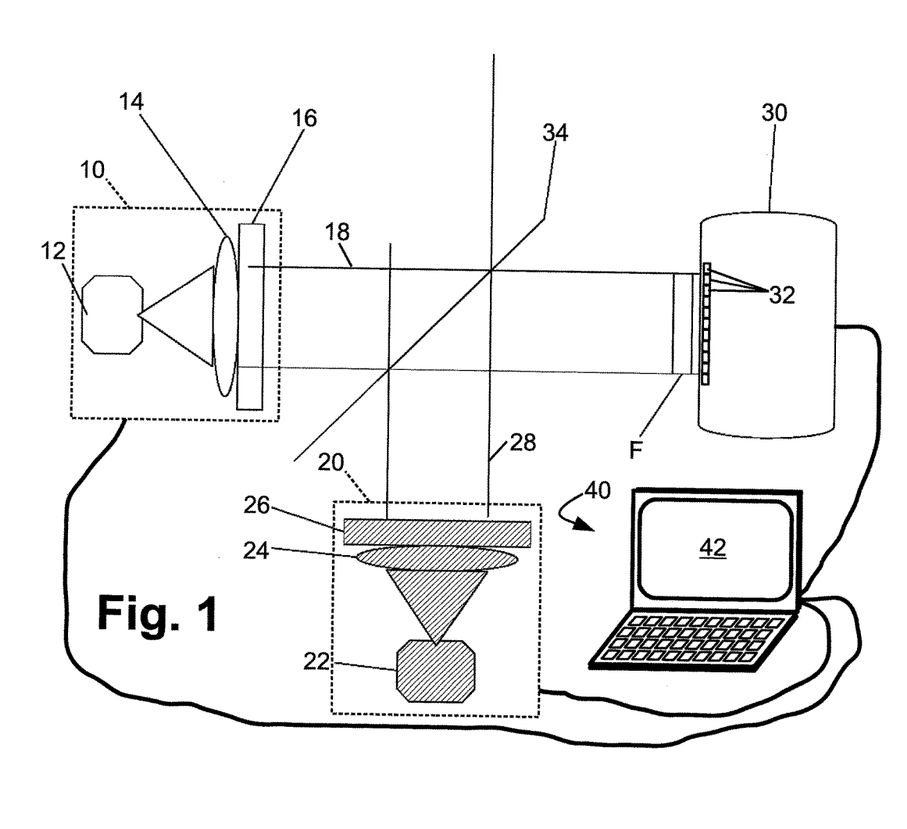
FIG. 1 diagrammatically shows a testing system for characterizing point flaws (including point defects and pinholes) in a filter under test.

With reference to FIG. 1, an illustrative testing device for testing an optical filter F for point flaws is described. The testing device includes a passband illumination source 10 comprising a light emitting element 12 such as an incandescent lamp, fluorescent lamp, light emitting diode (LED), laser, or so forth. The passband illumination source 10 may optionally include further components such as one or more optional beam-forming optical elements 14 (e.g. an illustrative collimating lens or set of lenses) and one or more optional spectrum-shaping elements such as an illustrative trimming filter 16. The passband illumination source 10 is configured to output passband illumination 18 with a beam area encompassing the area of the filter F under test, and whose spectral range lies entirely within (or at least overlaps) the passband of the filter F under test. In one example, the light emitting element is an LED whose light is collimated by the lens 14. In this example the LED produces a substantially monochromatic output which is chosen to be in the passband of the filter F, and the filter 16 is either omitted or used to remove any tail from the primarily monochromatic output of the LED. In another example, the light emitting element 12 is a halogen lamp producing a broadband output and the filter 16 is a bandpass filter whose passband is within the passband of the filter F under test. These are merely examples.

The testing device further includes a stopband illumination source 20 comprising a light emitting element 22 such as an incandescent lamp, fluorescent lamp, light emitting diode (LED), laser, or so forth. The stopband illumination source 20 may optionally include further components such as one or more optional beam-forming optical elements 24 (e.g. an illustrative collimating lens or set of lenses) and one or more optional spectrum-shaping elements such as an illustrative trimming filter 26. The stopband illumination source 20 is configured to output stopband illumination 28 with a beam area encompassing the area of the filter F under test, and whose spectral range lies entirely outside of the passband of the filter F under test and within the stopband of the filter F under test. In one example, the light emitting element is an LED whose light is collimated by the lens 24. In this example the LED produces a substantially monochromatic output which is chosen to be in the stopband of the filter F, and the filter 26 is either omitted or used to remove any portion of the spectrum that lies within the passband of the filter F from the primarily monochromatic output of the LED. In another example, the light emitting element 22 is a halogen lamp producing a broadband output and the filter 26 is a bandpass filter whose passband is entirely outside the passband of the filter F and preferably entirely within the stopband of the filter F. These again are merely examples.

The testing device of FIG. 1 further includes a photodetector element 30 which includes a two-dimensional array of photodetectors 32. (In FIG. 1 the detector array 30 is schematically shown in side view with the second dimension "oriented into the page"). The photodetectors 32 are broadband detectors insofar as they are at least capable of detecting both the passband illumination 18 and the stopband illumination 28. An optical multiplexing component or sub-system 34 is configured to couple the passband illumination 18 and the stopband illumination 28 to illuminate the filter F under test in a transmission geometry in which the illumination 18, 28 passes through the filter F under test (if it is transmissive for the light) and impinges on the array of photodetectors 32. In the illustrative testing device of FIG. 1 the optical multiplexing component or sub-system 34 is a beam splitter/combiner, although more complex multiplexing arrangements are contemplated. The array of photodetectors 32 is preferably wide enough to span the active area of the filter F under test. If the filter F is too large to be accommodated by the area of the array of photodetectors 32 then a mechanical stage can be used to position various areas of the filter F under test allowing the entire surface to be mapped. The spatial resolution of the point flaw characterization is determined by the size of the photodetectors 32, i.e. for a given area an array of a higher number of smaller photodetectors provides better spatial resolution than an array of a smaller number of larger photodetectors. Each individual photodetector of the array of photodetectors 32 may thus be considered a pixel of an image generated by the array of photodetectors 32. By way of some illustrative examples, the array of photodetectors 32 may be an array of charge-coupled devices (CCDs) and the photodetector element 30 is then a CCD camera. As another example, the photodetector element 30 could be a CMOS imager with a CMOS detector array. These are merely illustrative examples.

In the illustrative embodiment, the filter F under test is placed parallel with and in close proximity to the array of photodetectors 32. Indeed in one embodiment it is contemplated to orient the array of photodetectors 32 and to lay the filter F directly on top of the array of photodetectors 32. This approach is suitable if the active area of the filter F under test is of a size comparable with the area of the array of photodetectors 32. On the other hand, if these areas are different then the array of photodetectors 32 may be spaced apart from the filter F under test and suitable intervening magnifying/imaging optics (not shown) employed to form an image (optionally with size magnification or reduction) of the filter on the array of photodetectors.

In some embodiments, a collimated geometry for the illumination 18, 28 (or another illumination geometry with specific directional, angular, convergence, divergence, or other characteristics) is contemplated. For example, the filter F may include collimating entrance/exit apertures, and/or an interference filter having a narrow operational angular range, or so forth, and for such a filter-under-test the geometry/characteristics of the illumination 18, 28 should match those of the illumination that will be applied to the filter in its intended application.

The testing device of FIG. 1 still further includes an electronic controller 40, e.g. an illustrative computer, which is programmed to turn the illumination sources 10, 20 on or off and to read data from the photodetector element 30. Control of the illumination sources 10, 20 may be achieved by turning the respective light emitting elements 12, 22 on or off as appropriate, or by operating an optical shutter (not shown). The electronic controller preferably includes a display component 42, such as the illustrative computer display, for displaying results of the point flaw test performed on the filter F by the testing device of FIG. 1. These results may, for example, include a spatial map of the active area of the optical filter F point flaws indicated by suitable symbols, or an actual image produced by the array of detectors 32, i.e. a two-dimensional plot of all intensity values measured by the array of detectors 32. The displayed results may also include statistical values, for example a count of point flaws per unit area, or the total count of point flaws over the entire active area of the filter F. Moreover, since as will be described the testing distinguishes between pinholes and point defects, these may be separately displayed as separate maps and count values.

Figure 2:
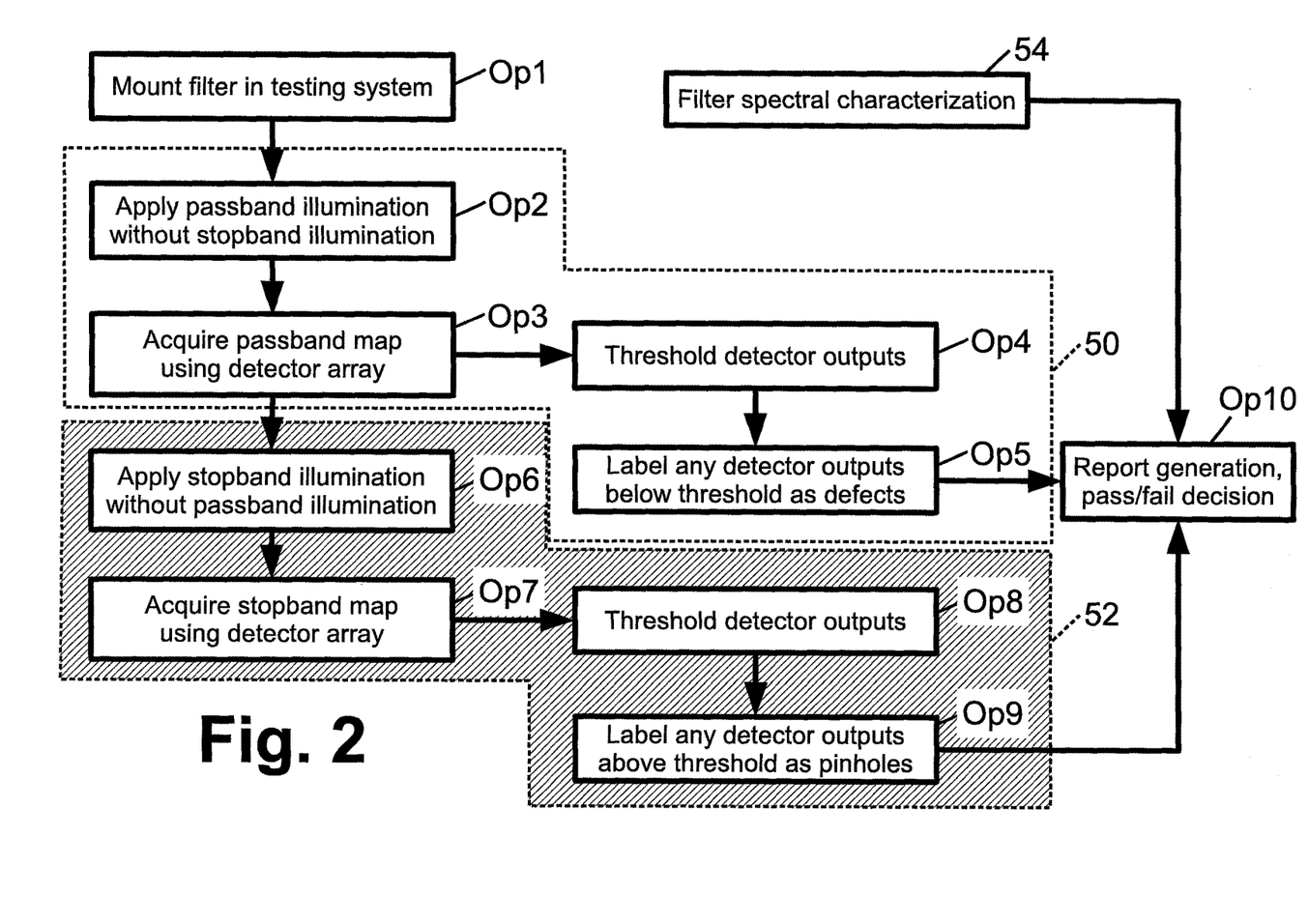
FIG. 2 diagrammatically shows a testing process for characterizing point flaws suitably performed using the filter testing system of FIG. 1.

With continuing reference to FIG. 1 and further reference to FIG. 2, a testing process is described for characterizing point flaws in the optical filter F using the testing device of FIG. 1. In an operation Op1, the filter F under test is mounted in the testing apparatus of FIG. 1, e.g. by placing the filter in contact with the array of photodetectors in an embodiment in which the array is horizontal, or using suitable mounting brackets or clamps in other embodiments. Thereafter, a passband test 50 is performed followed by a stopband test 52. It will be appreciated that the order of these two tests can be reversed, i.e. the stopband test 52 could be performed first followed by the passband test 50. Each test 50, 52 is described in sequel in the following.

The illustrative passband test 50 includes operations Op2, Op3, Op4, Op5. In operation Op2, the passband illumination 18 is applied without the stopband illumination 28. To this end, the control device 40 turns on (unshutters) the passband illumination source 10 and turns off (or shutters off) the stopband illumination source 20. With the passband illumination 18 on and the stopband illumination 28 off, the optical multiplexing component or sub-system 34 illuminates the filter F under test with only the passband illumination 18. Since the spectral extent of this passband illumination 18 is within (or overlaps) the passband of the filter F under test, the entire active area of the filter F should transmit the illumination 18 (or the spectral portion thereof in the filter passband) to the array of photodetectors 32. However, if there is a point defect at some location of the filter F, then the passband illumination 18 will be blocked by that point defect. In operation Op3, the electronic control device 40 reads the photodetector element 30, and more particularly the array of photodetectors 32, in order to acquire a passband map which should be entirely bright (i.e. illuminated) in the absence of any point defects. In operation Op4 the electronic control device 40 processes the in order to acquire a passband map to identify any point defects. A straightforward approach for this processing is to threshold the intensity output of each photodetector (i.e. each pixel of the passband map) and, in operation Op5, any detector output (i.e. pixel value) that falls below the point defect threshold intensity is labeled as a point defect. Optionally, operation Op4 may employ more complex processing, such as first computing the point defect threshold intensity based on the average measured photodetector intensity (i.e. average pixel intensity over the image) obtained in the operation Op3. Assuming that point defects are low in number and of low density, this average intensity will be close to the intensity transmitted by a "good" region of the filter F, and so the point defect threshold intensity can be set below this average value, e.g. to 50% of the average value in some embodiments. Optionally, the operation Op5 may further include a grouping or connectivity analysis of the pixels identified as point defects, in which contiguous groups of pixels indicated as being point defects by the thresholding operation Op4 are grouped together and labeled as a single (larger) point defect.

Likewise, the illustrative stopband test 52 includes operations Op6, Op7, Op8, Op9. In operation Op6, the stopband illumination 28 is applied without the passband illumination 18. To this end, the control device 40 turns on (unshutters) the stopband illumination source 20 and turns off (or shutters off) the passband illumination source 10. With the stopband illumination 28 on and the passband illumination 18 off, the optical multiplexing component or sub-system 34 illuminates the filter F under test with only the stopband illumination 28. Since the spectral extent of this stopband illumination 18 is entirely outside of the passband of the filter F under test, and preferably entirely within the stopband of the filter F, the illumination 28 should be entirely blocked over the entire active area of the filter F. However, if there is a pinhole at some location of the filter F, then the stopband illumination 28 will be transmitted via that pinhole. In operation Op7, the electronic control device 40 reads the photodetector element 30, and more particularly the array of photodetectors 32, to acquire a stopband map which should be entirely dark (i.e. unilluminated) in the absence of any pinholes. In operation Op8 the electronic control device 40 processes the stopband map to identify any pinholes. A straightforward approach for this processing is to threshold the intensity output of each photodetector (i.e. each pixel of the stopband map) and, in operation Op9, any detector output (i.e. pixel value) that is above the pinhole threshold intensity is labeled as a pinhole. Optionally, operation Op8 may employ more complex processing, such as first computing the pinhole threshold intensity based on the average measured photodetector intensity (i.e. average pixel intensity over the image) obtained in the operation Op3. Assuming that pinholes are low in number and of low density, this average intensity will be close to zero, and the pinhole threshold intensity can be set a few percent above this near-zero average value. Optionally, the operation Op9 may further include a grouping or connectivity analysis of the pixels identified as pinholes, in which contiguous groups of pixels indicated as being pinholes by the thresholding operation Op8 are grouped together and labeled as a single (larger) pinhole.

It will be appreciated that the operations Op4, Op5, Op8, and Op9 should be performed only for those detector elements of the array of detector elements 32 that are mapping the active area of the filter F. That is, if the active area of the filter F (or the magnified or reduced active area of the image of the filter F at the array 32) is smaller than the area of the array 32, then those detectors outside this area are ignored. The active area can be identified in various ways, such as by a pre-calibration of the area or by identifying the active area boundary in the passband and/or stopband images. For example, if the filter is opaque outside of its active area, then in the passband image the boundary of the active area will be defined by a sharp transition from illuminated to unilluminated, and this can be detected to identify the edges of the active area.

With continuing reference to FIG. 2, the output of the passband test 50 is a map of the point defects, while the output of the stopband test 52 is a map of the pinholes. This information is input to a reporting/grading operation Op10 which may optionally also receive information from other filter tests such as a filter spectral characterization test 54 (e.g. spectral measurements over the design-basis spectrum performed at one or more locations of the filter F using a spectral characterization apparatus that is different from the point flaws testing device of FIG. 1). As previously mentioned, the operation Op10 may report results in a variety of ways, such as by displaying maps of point defects and pinholes, respectively, on the display component 42, and/or computing a percentage of the pixels of the passband and stopband maps acquired in respective operations Op3, Op7 which are labeled as point defects and pinholes respectively, or so forth. The operation Op10 may additionally grade the filter F under test, for example assigning a passing grade to the filter F only if (1) the results of the filter spectral characterization test 54 meet the filter specification and (2) the count of point defects is below a maximum value (which may be specified as part of the filter specification) and (3) the count of pinholes is below a maximum value (which again may be specified as part of the filter specification). Other factors for grading the filter F under test may include the size of the largest point defect and of the largest pinhole (obtainable if the respective operations Op5, Op9 include aggregation of contiguous labeled pixels), with the filter F failing if one or both of these sizes exceeds some maximum allowable size In another application of the test system of FIGS. 1 and 2, the filter F under test is a single wafer or substrate that contains a large number of small filter elements. For example, the filter F under test may be a wafer-level filter that, in a later stage of processing, will be diced or separated into a large number of individual (small) filter elements. In this case the map identifies those filter elements with and without defects, so that they can be separated during subsequent processing (e.g., discarding those filter elements identified as defective in the wafer-level testing performed in accord with FIG. 2 using the system of FIG. 1).

Figure 3:
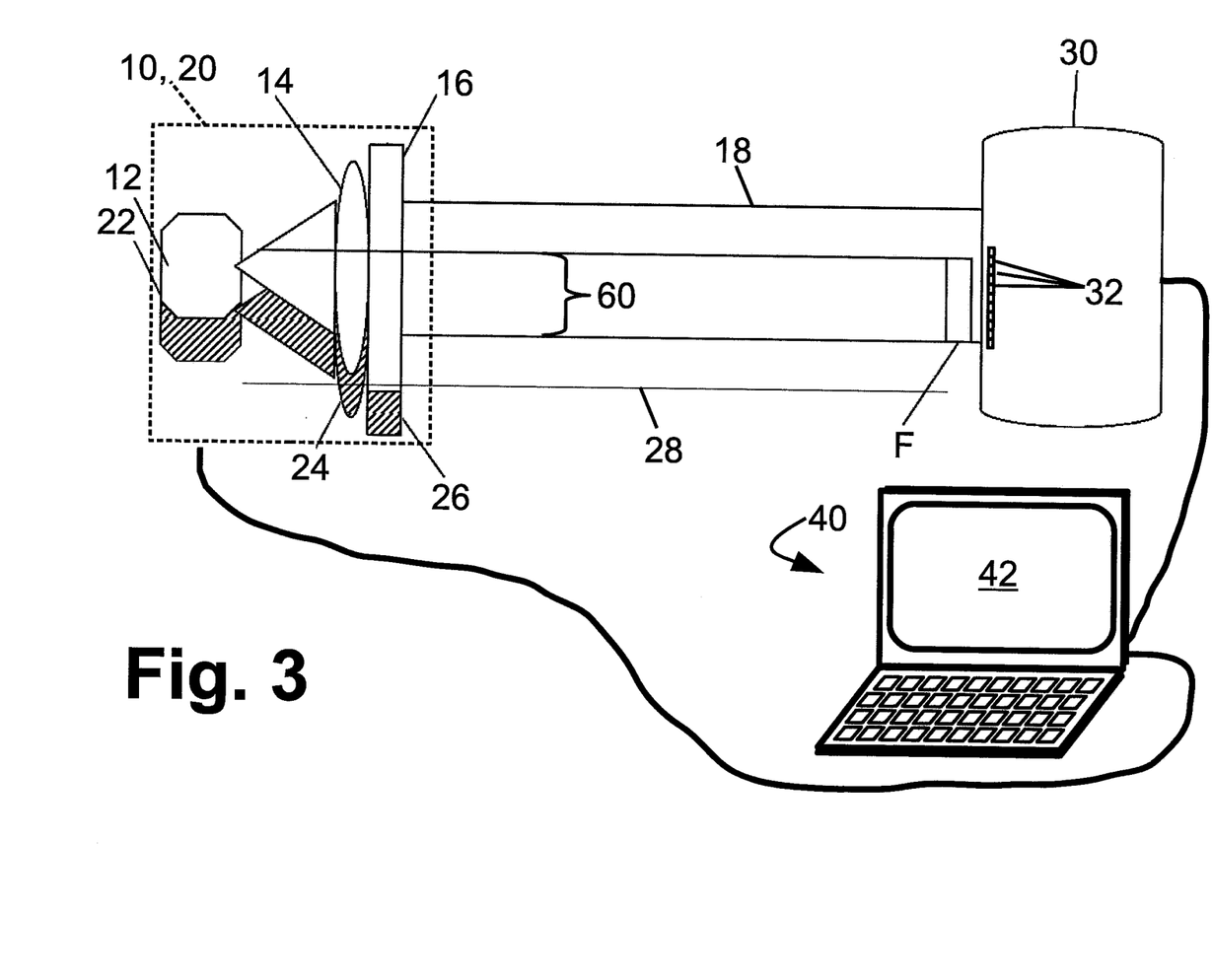
FIGS. 3-6 diagrammatically show alternative embodiments of the testing system of FIG. 1.
Figure 4:
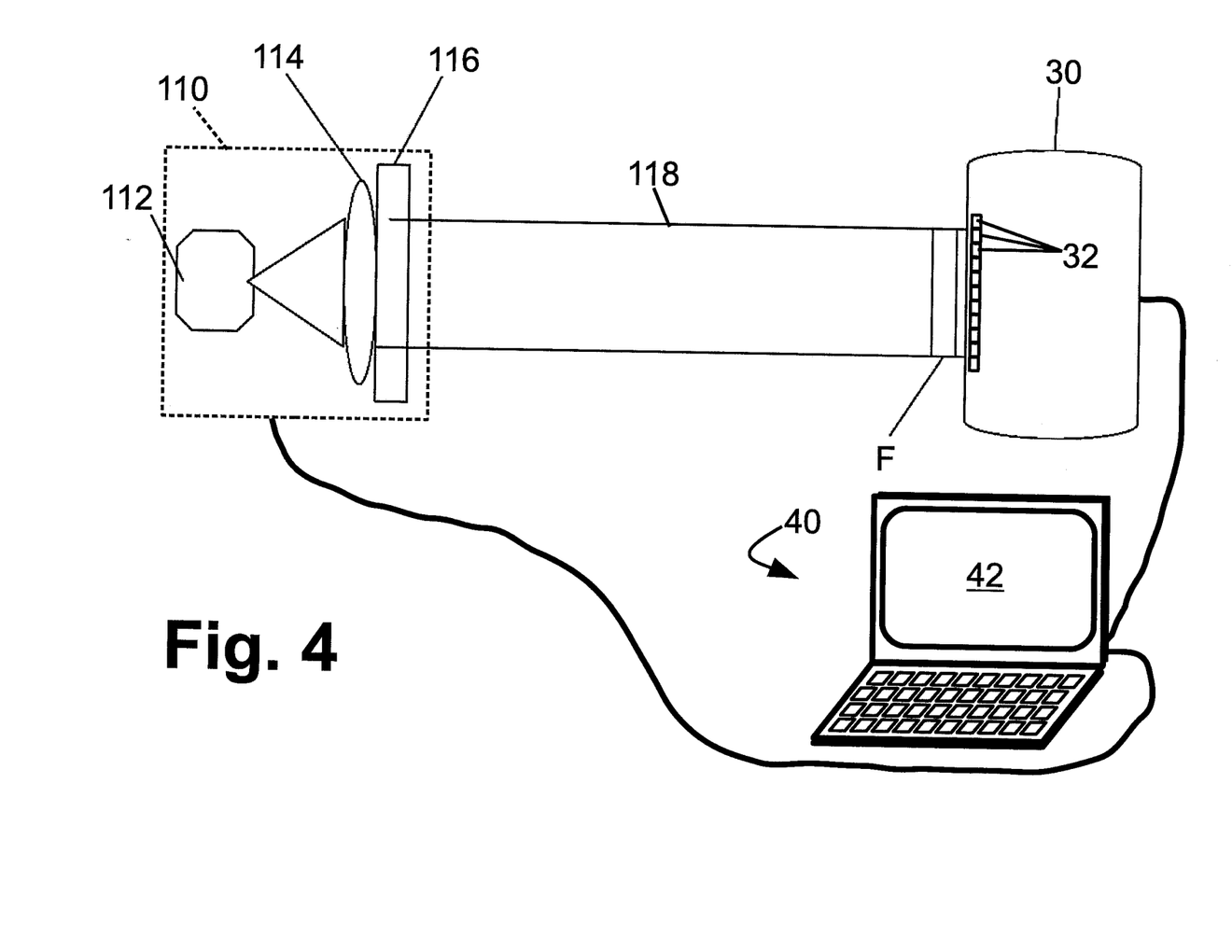

With reference to FIGS. 3 and 4, some illustrative alternative configurations for the testing device are described. The testing device of FIG. 3 includes most of the same components as that of FIG. 1, and in particular includes passband illumination source 10 comprising light emitting element 12, optional beam-forming optical element(s) 14, and optional spectrum-shaping element(s) 16 cooperatively producing output passband illumination 18; and stopband illumination source 20 comprising light emitting element 22, optional beam-forming optical element(s) 24, and optional spectrum-shaping element(s) 26 cooperatively producing output stopband illumination 28; and photodetector element 30 with two-dimensional array of photodetectors 32; and electronic controller 40 with display component 42. However, the testing device of FIG. 3 omits the optical multiplexing component or sub-system 34 in favor of a laterally offset arrangement of the two illumination sources 10, 20 which produces the respective passband illumination 18 and stopband illumination 28 whose beam widths overlap over a common beam area 60 that is large enough to span the entire active area of the filter F under test. Depending upon spectral characteristics, the two illumination sources 10, 20 may optionally share one or more beam-forming elements and/or one or more spectrum-shaping elements. The testing system of FIG. 3 can be employed using the same method as that described previously with reference to FIG. 2.

It is to be appreciated that FIGS. 1 and 3 are merely illustrative examples, and other optical configurations can be employed to selectively apply the passband illumination 18 from the passband illumination source 10, or the stopband illumination 28 from the stopband illumination source 20, to the optical filter F under test.

With reference to FIG. 4, in another variant test device, a single illumination source 110 replaces both illumination sources 10, 20. The single illumination source 110 again includes a light emitting element 112, optional beam-forming optical element(s) 114, and optional spectrum-shaping element(s) 116 that cooperatively produce output illumination 118 which illuminates the filter F under test and, after transmission (where it occurs in view of the passband/stopband configuration of the filter F as further impacted by any point flaws) is detected by the photodetector element 30 with two-dimensional array of photodetectors 32 and analyzed by the electronic controller 40 with display component 42. The test device configuration of FIG. 4 with its single illumination source 110 can be employed in various ways, some non-limiting examples of which are set forth in the following. In one approach, the light emitting element 112 is switchable between emitting illumination 118 in the passband of the filter F under test and in the stopband of the filter F under test. In this approach, the test device of FIG. 4 can execute the point flaws test method of FIG. 2, except that operation Op2 entails switching the light emitting element 112 to emit passband illumination and operation Op6 entails switching the light emitting element 112 to emit stopband illumination.

Figure 5:
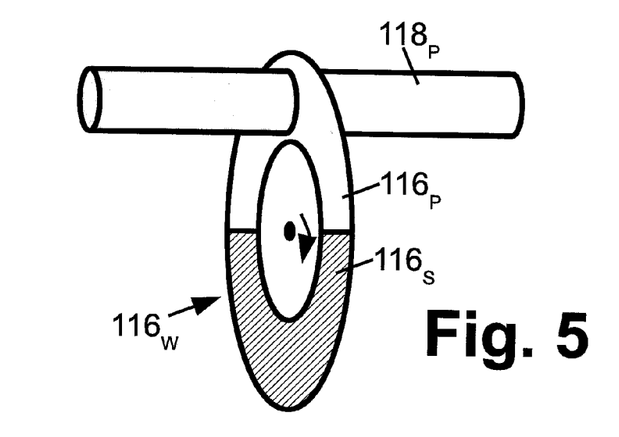
Figure 6:
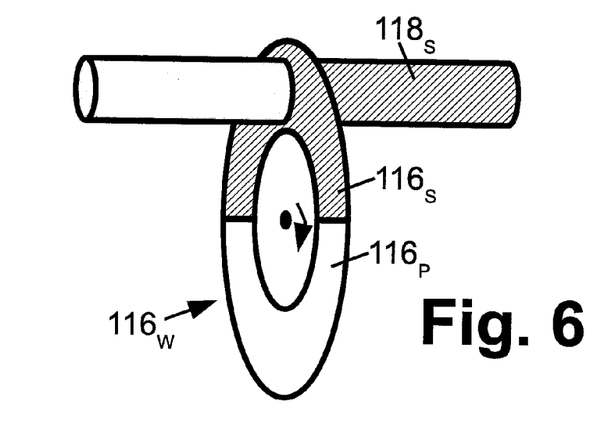

With continuing reference to FIG. 4 and with further reference to FIGS. 5 and 6, in another configuration of the test device of FIG. 4, the light emitting element 112 emits broadband illumination over a spectral range that encompasses (or at least overlaps) both the passband and the stopband of the optical filter F under test. In this illustrative configuration, the spectrum-shaping element(s) 116 include a switchable spectral filter that selectively emits light in the passband or stopband of the filter F. In one illustrative example (FIGS. 5 and 6), the switchable spectrum-shaping element(s) 116 include a rotating filter wheel $116_W$ with a passband filter section $116_P$ and a stopband filter section $116_S$. When rotation of the filter wheel $116_W$ brings the passband filter section $116_P$ into intersection with broadband illumination from the broadband light emitting element 112, the output illumination which illuminates the filter F under test is the passband illumination $118_P$ (FIG. 5); whereas, when rotation of the filter wheel $116_W$ brings the stopband filter section $116_S$ into intersection with broadband illumination from the broadband light emitting element 112, the output illumination which illuminates the filter F under test is the stopband illumination $118_S$ (FIG. 6). The configuration also can perform the method of FIG. 2, except that when using the apparatus of FIGS. 4-6 the operation Op2 is effectuated by rotation of the filter wheel $116_W$ into the position shown in FIG. 5 and the operation Op6 is effectuated by rotation of the filter wheel $116_W$ into the position shown in FIG. 6. In one suitable approach, the filter wheel $116_W$ rotates continuously and in an open-loop fashion, and operations Op2, Op6 are performed by real-time analysis of the integrated signal output by the photodetector element 30—with the filter wheel $116_W$ in the position of FIG. 5 the summed output of the array of photodetectors 32 will be high and in this state operation Op3 is performed to acquire the passband map, while when the filter wheel $116_W$ rotates to the position of FIG. 6 the summed output of the array of photodetectors 32 will be low and in this state operation Op7 is performed to acquire the stopband map. While the illustrative filter wheel $116_W$ has two sections $116_P$, $116_S$ each spanning 180° of the filter wheel $116_W$, in other embodiments there may be, e.g. four alternating sections: a passband filter section spanning 90° followed by a stopband filter section spanning 90° followed by a passband filter section spanning 90° followed by a stopband filter section spanning 90°.

In another contemplated configuration of the test device of FIG. 4, one instance of the test device of FIG. 4 is used to perform only the test 50 for pinholes, in which case the single illumination source 110 is suitably equivalent to the passband illumination source 10 of FIGS. 1 and 3; and, another instance of the test device of FIG. 4 is used to perform only the test 52 for point defects, in which case the single illumination source 110 is suitably equivalent to the stopband illumination source 20 of FIGS. 1 and 3. In this embodiment, the filter F under test is suitably first inserted into the passband test device to perform the passband test, and then inserted into the stopband test device to perform the stopband test (or, this test order may be reversed).

With returning reference to FIG. 2 and with reference generally to the disclosure herein, it will be appreciated that in performing the method of FIG. 2 the test device should be configured to not simultaneously apply both the passband illumination and the stopband illumination. As described with reference to FIG. 2, the optical filter F under test is illuminated with only the passband illumination (via operation Op2) during the passband test 50; and similarly the optical filter F under test is illuminated with only the stopband illumination (via operation Op6) during the stopband test 52. Moreover, the passband illumination should have a spectral range that at least overlaps a passband of the optical filter under test; and similarly the stopband illumination should have a spectral range that lies entirely outside of the passband of the optical filter under test (and preferably lies within the design-basis spectrum of the optical filter under test). In some embodiments the passband illumination and/or the stopband illumination may be monochromatic. The two-dimensional array of photodetectors 32 is arranged to detect the passband illumination after passing through the filter under test and to detect the stopband illumination after passing through the filter under test.

Advantageously, illustrative embodiments of the test devices disclosed herein for characterizing for point flaws of an optical filter under test (including pinholes and point defects) does not acquire any spectral data for the optical filter under test, and hence the point flaws test is efficient. Optionally, as indicated by filter spectral characterization operation 54 of FIG. 2, another test device used to perform the filter spectral characterization operation 54 does acquire spectral data for the optical filter under test—this other test device typically acquires spectral data at one, or at most a few, discrete points over the area of the filter under test, and hence is not efficient at detecting or characterizing point flaws of the filter under test. It is thus appreciated that the disclosed test devices for characterizing point flaws (e.g. devices of FIG. 1, 3, or 4 performing the method of FIG. 2 or a variant thereof) operate synergistically with a conventional optical filter spectral characterization test device (e.g., including a spectrometer or spectrograph) to more completely characterize the optical filter under test respective to both to confirm the filter specification is met (e.g. passband center wavelength and FWHM, cutoff slope, et cetera) and to ensure the optical filter is not defective due to a high number, density, and/or size of point flaws (stopband light-transmissive pinholes and/or passband light-blocking point defects).

It will be appreciated that various of the above-disclosed and other features and functions, or alternatives thereof, may be desirably combined into many other different systems or applications. It will be further appreciated that various presently unforeseen or unanticipated alternatives, modifications, variations or improvements therein may be subsequently made by those skilled in the art which are also intended to be encompassed by the following claims.

The invention claimed is:

1. A test device for characterizing point flaws of an optical filter under test including pinholes and point defects, the test device comprising:
   a passband illumination source configured to illuminate the optical filter under test with passband illumination whose spectral range at least overlaps a passband of the optical filter under test;
   a stopband illumination source configured to illuminate the optical filter under test with stopband illumination whose spectral range lies entirely outside of the passband of the optical filter under test;
   a two-dimensional array of photodetectors arranged to detect the passband illumination after passing through the optical filter under test and to detect the stopband illumination after passing through the optical filter under test; and
   an electronic controller configured to operate in conjunction with the passband illumination source, the stopband illumination source, and the two-dimensional array of photodetectors to:
      perform a passband test including acquiring a passband map of the optical filter under test using the two-dimensional array of photodetectors while illuminating the optical filter under test with the passband illumination and not illuminating the optical filter under test with the stopband illumination, and
      perform a stopband test including acquiring a stopband map of the optical filter under test using the two-dimensional array of photodetectors while illuminating the optical filter under test with the stopband illumination and not illuminating the optical filter under test with the passband illumination.

2. The test device of claim 1 wherein the test device is configured to not simultaneously illuminate the optical filter under test with both the passband illumination and the stopband illumination.

3. The test device of claim 1 wherein:
   the electronic controller is configured to perform the passband test further including identifying point defects as locations of the passband map of the optical filter under test where the intensity is below a point defect threshold intensity; and
   wherein the electronic controller is configured to perform the stopband test further including identifying pinholes as locations of the stopband map of the optical filter under test where the intensity is above a pinhole threshold intensity.

4. The test device of claim 3 further comprising:
   a display component;
   wherein the electronic controller configured to perform the passband test further including displaying one of the passband map and a map of the identified point defects on the display component; and
   wherein the electronic controller configured to perform the stopband test further including displaying one of the stopband map and a map of the identified pinholes on the display component.

5. The test device of claim 3 wherein:
   the electronic controller configured to perform the passband test further including computing statistics for the identified point defects and displaying the computed point defects statistics on a display component of the electronic controller; and
   the electronic controller configured to perform the stopband test further including computing statistics for the identified pinholes and displaying the computed pinhole statistics on the display component of the electronic controller.

6. The test device of claim 3 wherein:
   the identifying of point defects includes aggregating contiguous pixels of the passband map whose intensities are below the point defect threshold intensity to identify a point defect as the aggregation of contiguous pixels; and
   the identifying of pinholes includes aggregating contiguous pixels of the stopband map whose intensities are above the pinhole threshold intensity to identify a pinhole as the aggregation of contiguous pixels.

7. The test device of claim 1 wherein:
   the passband illumination source is configured to output only the passband illumination whose spectral range at least overlaps the passband of the optical filter under test;
   the stopband illumination source is configured to output only the stopband illumination whose spectral range lies entirely outside of the passband of the optical filter under test;
   the test device further includes an optical multiplexing component or sub-system configured to couple the passband illumination to illuminate the optical filter under test and to couple the stopband illumination to illuminate the optical filter under test;
   the electronic controller is configured to perform the passband test including operating the passband illumination source to output the passband illumination and operating the stopband illumination source to not output the stopband illumination; and
   the electronic controller is configured to perform the stopband test including operating the stopband illumination source to output the stopband illumination and operating the passband illumination source to not output the passband illumination.

8. The test device of claim 1 wherein:
   the passband illumination source includes:
      a broadband light source outputting a broadband illumination whose spectral range includes both the spectral range of the passband illumination and the spectral range of the stopband illumination; and
      a passband filter configured to pass the passband illumination and block the stopband illumination;
   the stopband illumination source includes:
      the broadband light source; and
      a stopband filter configured to pass the stopband illumination and block the passband illumination;
   the electronic controller is configured to perform the passband test with the passband filter arranged to filter the broadband illumination output by the broadband light source to illuminate the optical filter under test with the passband illumination; and the electronic controller is configured to perform the stopband test with the stopband filter arranged to filter the broadband illumination output by the broadband light source to illuminate the optical filter under test with the stopband illumination.

9. The test device of claim 1 wherein the test device is not configured to acquire any spectral data for the optical filter under test.

10. The test device of claim 1 wherein the test device does not include a spectrometer or spectrograph.

11. A test method for characterizing point flaws of an optical filter under test including pinholes and point defects, the test method comprising:
performing a passband test including:
illuminating the optical filter under test with passband illumination whose spectral range at least overlaps a passband of the optical filter under test and
acquiring a passband map of the optical filter under test using a two-dimensional array of photodetectors while illuminating the optical filter under test with the passband illumination and
using an electronic controller, identifying point defects of the optical filter under test as low intensity locations of the passband map; and
performing a stopband test including:
illuminating the optical filter under test with stopband illumination whose spectral range lies entirely outside of the passband of the optical filter under test and
acquiring a stopband map of the optical filter under test using the two-dimensional array of photodetectors while illuminating the optical filter under test with the stopband illumination and
using the electronic controller, identifying pinholes of the optical filter under test as high intensity locations of the stopband map.

12. The test method of claim 11 wherein:
the performing of the passband test does not include illuminating the optical filter under test with the stopband illumination; and
the performing of the stopband test does not include illuminating the optical filter under test with the passband illumination.

13. The test method of claim 11 further comprising:
displaying one of the passband map and a map of the identified point defects on a display component; and
displaying one of the stopband map and a map of the identified pinholes on the display component.

14. The test method of claim 11 further comprising:
using the electronic controller, computing statistics for the identified point defects and displaying the computed point defects statistics on a display component; and
using the electronic controller, computing statistics for the identified pinholes and displaying the computed pinhole statistics on the display component.

15. The test method of claim 11 wherein:
the identifying of point defects includes aggregating contiguous pixels of the passband map whose intensities are below the point defect threshold intensity to identify point defects as aggregations of contiguous pixels whose intensities are below the point defect threshold intensity; and
the identifying of pinholes includes aggregating contiguous pixels of the stopband map whose intensities are above the pinhole threshold intensity to identify pinholes as aggregations of contiguous pixels whose intensities are above the pinhole threshold intensity.

16. The test method of claim 11 wherein:
illuminating the optical filter under test with passband illumination includes turning on or shuttering on a passband illumination source that outputs the passband illumination while turning off or shuttering off a stopband illumination source that outputs the stopband illumination; and
illuminating the optical filter under test with stopband illumination includes turning on or shuttering on the stopband illumination source while turning off or shuttering off the passband illumination source.

17. The test method of claim 11 wherein:
illuminating the optical filter under test with passband illumination includes illuminating the optical filter under test with broadband illumination filtered by a passband filter that passes the passband illumination while blocking the stopband illumination; and
illuminating the optical filter under test with stopband illumination includes illuminating the optical filter under test with broadband illumination filtered by a stopband filter that passes the stopband illumination while blocking the passband illumination.

18. The test method of claim 11 wherein the test method does not include acquiring any spectral data for the optical filter under test.

19. A test device for characterizing point flaws of an optical filter under test including pinholes and point defects, the test device comprising:
an illumination source configured to illuminate the optical filter under test with passband illumination whose spectral range at least overlaps a passband of the optical filter under test;
an array of photodetectors arranged to acquire a passband map of the optical filter under test while illuminating the optical filter under test with the passband illumination;
an illumination source configured to illuminate the optical filter under test with stopband illumination whose spectral range lies entirely outside of the passband of the optical filter under test;
wherein the array of photodetectors is further arranged to acquire a stopband map of the optical filter under test using the two-dimensional array of photodetectors while illuminating the optical filter under test with the stopband illumination; and
an electronic controller programmed to:
identify point defects of the optical filter under test as low intensity locations of the passband map; and
identify pinholes of the optical filter under test as high intensity locations of the stopband map.

* * * * *